United States Patent [19]

McCormick

[11] 4,267,281
[45] May 12, 1981

[54] CONTROLLED RELEASE PESTICIDES

[76] Inventor: Charles L. McCormick, 2308 Clayton Pl., Hattiesburg, Miss. 39401

[*] Notice: The portion of the term of this patent subsequent to May 12, 1998, has been disclaimed.

[21] Appl. No.: 59,570

[22] Filed: Jul. 20, 1979

Related U.S. Application Data

[63] Continuation-in-part of Ser. No. 766,522, Feb. 7, 1977, abandoned, and Ser. No. 820,956, Aug. 1, 1977, abandoned.

[51] Int. Cl.³ .............................................. C08F 8/32
[52] U.S. Cl. .................................. 525/61; 71/DIG. 1; 71/93; 71/117; 260/112.5; 424/19; 424/78; 424/93; 424/358; 526/301; 536/2; 536/31; 536/45; 536/51; 536/55
[58] Field of Search ............... 525/61; 71/DIG. 1, 93, 71/117; 424/19, 358, 78

[56] References Cited

U.S. PATENT DOCUMENTS

| | | | |
|---|---|---|---|
| 3,213,236 | 10/1965 | Allan | 71/DIG. 1 |
| 3,470,148 | 9/1967 | Allan | 71/DIG. 1 |
| 3,485,806 | 12/1967 | Bloomquist et al. | 71/85 |
| 3,539,373 | 11/1970 | Cooke | 71/DIG. 1 |
| 3,619,371 | 11/1971 | Crook et al. | 526/9 |
| 3,761,936 | 6/1976 | Westphal et al. | 71/93 |

FOREIGN PATENT DOCUMENTS

| | | |
|---|---|---|
| 85468 | 10/1971 | German Democratic Rep. |
| 47-19200 | 6/1972 | Japan |
| 49-8263 | 2/1974 | Japan |
| 1242151 | 8/1971 | United Kingdom |

OTHER PUBLICATIONS

CA 78, 125374s (1973).
J. Agr. Food Chem., 24, pp. 666–668 (1976).

Primary Examiner—Stanford M. Levin
Attorney, Agent, or Firm—Quarles & Brady

[57] ABSTRACT

Controlled release pesticides are prepared by reacting an isocyanate derivative of a pesticide with a polymer having pendant groups containing a reactive hydrogen to obtain a novel pesticide-polymer system in which the pesticide is chemically bonded to the polymer. Active pesticidal material is released from the pesticide-polymer system by hydrolysis or chemical depolymerization under conditions of use.

5 Claims, No Drawings

CONTROLLED RELEASE PESTICIDES

RELATED APPLICATION

This is a continuation-in-part application of my earlier applications, both abandoned, Ser. No. 766,522 filed Feb. 7, 1977, and titled "Controlled Release Pesticides and Method of Preparation" and Ser. No. 820,956 filed Aug. 1, 1977 and titled "Controlled Release Pesticides."

BACKGROUND OF THE INVENTION

In the past there have been numerous efforts made to develop controlled release or sustained release pesticides. One approach has been to entrap the pesticide in a protective polymeric coating such as, for example, the methods described in U.S. Pat. No. 3,569,769 and U.S. Pat. No. 3,269,900. Another approach has been to chemically couple the pesticide directly to a natural polymeric substrate such as lignin as described in Canadian Pat. No. 863,310 and still another approach has been to use a bridging compound to connect the pesticide to the natural polymeric substrate such as that described in Canadian Pat. No. 855,181. In addition, pesticides have been dissolved in waxes, incorporated in emulsions and combined with large amounts of inert carriers all in an effort to obtain sustained released pesticide compositions.

None of the above described approaches is completely without disadvantages. For example, entrapping the pesticide in a polymer is relatively expensive; the use of a natural polymer substrate may result in a product which is not only of a nonuniform consistency from batch to batch, but which is also bulky to transport and handle and the incorporation of pesticides in emulsions, waxes, and compositions including inert carriers may result in non-release or uneven release of the active ingredient.

SUMMARY OF THE INVENTION

It is the general object of the present invention to disclose a novel method of preparing novel, biodegradable, pesticide-polymer systems containing known pesticides which systems hydrolyze or depolymerize under conditions of use to yield active pesticidal materials.

It is a further object to disclose novel, biodegradable, pesticide-polymer systems that are hydrolyzed or depolymerized over a reasonable period of time to release the active pesticidal materials at a controlled rate.

In the preferred method of the present invention, an isocyanate derivative of a pesticide synthesized from a pesticide having an amino group is reacted with a polymer having pendant groups containing a reactive hydrogen to form a novel, biodegradable pesticide-polymer system which releases active pesticidal material at a controlled and sustained rate under conditions of use.

These and still other objects of the invention will be apparent to those skilled in the art from the disclosure which follows.

DESCRIPTION OF THE PREFERRED EMBODIMENT

The novel pesticide-polymer systems of the present invention may be represented by the following formula:

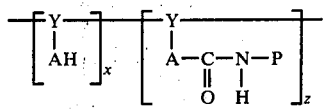

in which

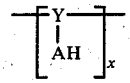

is the unreacted portion of a polymer of the formula

in which $x+z$ is from 5 to $1.0 \times 10^7$, x is less than $x+z$ and can be zero, A is the remainder of a reactive hydrogen containing pendant group of the formula AH from which the reactant hydrogen H has been removed. Although a single pendant AH group is shown, the repeating backbone of the polymer may contain up to 20 pendant groups and it is intended that AH be interpreted to include multiple groups. The extent of the reaction of the reactive hydrogen containing pendant groups of the polymer may range from about 1% to 100%. Representative of AH are such groups as —OH, —NH$_2$, —SH, —COOH, —CO$_3$H,

and —PO$_3$H. P is the pesticidal remainder of a pesticide and preferably a pesticide of the formula P—NH$_2$ from which P—NCO has been synthesized and Y represents the repeating structure of the macromolecular backbone of the polymer.

The novel pesticide-polymer systems of the present invention are preferably prepared by reacting a compound of the formula P—NCO, obtained from a pesticide of the formula PNH$_2$, with a polymer having a macromolecular backbone containing at least one pendant group containing a reactive hydrogen.

In the preferred practice of the invention, the isocyanate derivative of the pesticide is added to a solution of the polymer. The resulting mixture then is maintained under reaction conditions until the reaction is complete, e.g., about 1 to 4 hours at about 80°–120° C. The thus formed pesticide-polymer system is then isolated by conventional techniques.

The process may be represented as follows:

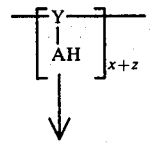

-continued

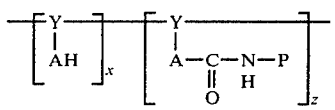

in which all symbols are as previously defined.

The term pesticide as employed herein is any active material used for biologic control of unwanted organisms including in particular insecticides, fungicides, herbicides, nematocides and other biocides, and including plant growth regulators and the like materials utilizable in a field environment.

The pesticides that may be used with the present invention are those pesticides which can be converted by known chemical methods to isocyanate derivatives which will react with the polymers to form pesticide-polymer systems that can be hydrolyzed or depolymerized under conditions of use to release active pesticidal materials. The pesticides especially preferred for use are those which include amino groups which are readily convertible to isocyanate derivatives by known chemical reactions.

Representative of the pesticides preferred for use in the present invention are the following:
3-amino-5-triazole
3-amino-2,5-dichlorobenzoic acid
4-amino-6-tert-butyl-3-(methylthio)-as-triazine-5(4H) one
4-amino-3,5-6-trichloropicolinic acid
5-amino-4-chloro-2-phenyl-3(2H)-pyridazinone
2-amino-3-chloro-1,4-naphthoquinone
4-amino pteroylglutamic acid
3-amino-2,5-dichlorobenzoic acid
4-amino-3,5,6-trichloropiodinic acid The pesticide which is especially preferred is 4-amino-6-tert-butyl-3-(methylthio)-as-triazine-5(4H) one which is available under the name Metribuzin.

Obviously, the foregoing list is not complete as other pesticides which can be modified to form isocyanate derivatives may be employed provided that the resulting pesticide-polymer system upon depolymerization yields an active pesticidal material.

The amino containing pesticides are preferably converted to the corresponding isocyanate derivatives by reacting the pesticide with phosgene under suitable reaction conditions as described in the literature. (See R. Morrison and R. Boyd, *Organic Chemistry*, 2nd Ed. 1966, pp. 926–927 and R. Fuson, *Reactions of Organic Compounds*, 1964, p. 337). Isocyanate derivatives also can be prepared from the corresponding amides using a Hoffman rearrangement. (See D. Grant and G. Hammond, *Organic Chemistry*, 2nd Ed. 1964, pp. 90 and 304).

In those instances in which the pesticide material contains other functional groups that may interfere with the selected reaction it may be desirable to first attach blocking groups to such functional groups and to later remove such blocking groups.

The polymers preferred for use in the invention may be represented by the formula:

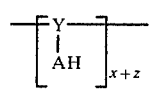

in which all symbols are as previously defined.

The polymers intended for use in the present invention, have reasonably discernible structures and molecular weights making it possible to prepare pesticide-polymer systems which can be tailored to contain a definite amount of releasable active pesticide material per unit of weight measure.

The polymer which is especially preferred is polyvinyl alcohol which is biodegradable and readily available commercially at reasonable cost. Polyvinyl alcohol is a polymer prepared from polyvinyl acetates by the replacement of the acetate groups with hydroxyl groups. Polyvinyl alcohol may be represented by the following formula:

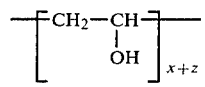

in which $x+z$ is $1 \times 10^2$ to $1 \times 10^7$.

Commercially available polyvinyl alcohols have different contents of residual acetyl groups, different molecular weights, and, therefore, different viscosity characteristics. Generally, the fist code number following the trade name indicates the degree of hydrolysis while the second set of numbers indicates the approximate viscosity and centipoise (4% aqueous solution at 20°). Among the polyvinyl alcohols that may be used in the method of the present invention are the low and high molecular weight polymers available at 100% solids from the Aldrich Chemical Company of Milwaukee, Wis.

Representatives of other polymers that may be represented by the formula

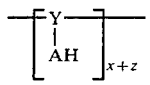

and which can be used in the present invention are:
Polyvinyl Alcohol-polyvinyl acetate copolymers
Polyacrylic Acid
Polymethacrylic Acid
Polyvinyl Amine
Cellulose and derivatives thereof such as:
  (1) hydroxy methyl cellulose,
  (2) hydroxy ethyl cellulose,
  (3) hydroxy propyl cellulose,
  (4) carboxymethyl cellulose,
  (5) xyanthate derivatives of cellulose
  (6) chitin and chitosans, and hydroxy-substituted polysaccharides such as starches, dextrans, xylans, and pectins.

The preparation of the preferred pesticide-polymer system from 4-isocyanato-6-tert-butyl-3-(methylthio)-astriazine-5(4H) one and the polyvinyl alcohol may be illustrated as follows:

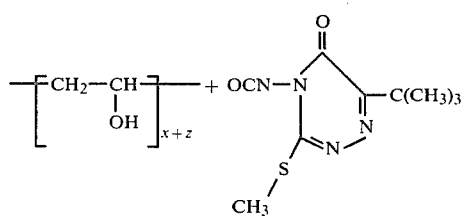

-continued

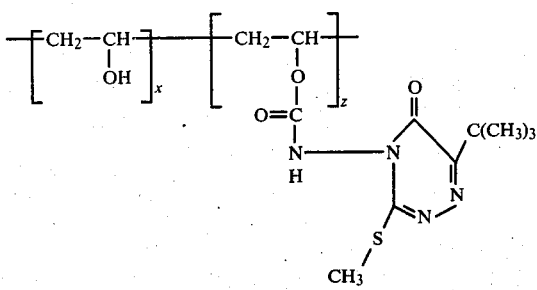

Preparation of other pesticide-polymer systems which can be obtained by exercise of the prepared methods of the present invention are those obtained by reacting the following:

4-isocyanato-6-tert-butyl-3-(methylthio)-as-triazine-5(4H) one and polyvinyl alcohol;
4-isocyanato-6-tert-butyl-3-(methylthio)-as-triazine-5(4H) one and cellulose;
4-isocyanato-6-tert-butyl-3-(methylthio)-as-triazine-5(4H) one and chitin;
4-isocyanato-6-tert-butyl-3-(methylthio)-as-triazine-5(4H) one and a 1:1 copolymer of polyvinyl alcohol and polyvinyl acetate;
4-isocyanato-6-tert-butyl-3-(methylthio)-as-triazine-5(4H) one and polyvinyl amine;
4-isocyanato-6-tert-butyl-3-(methylthio)-as-triazine-5(4H) one and dextran (average molecular weight 70,000);
3-isocyanato-2,5-dichlorobenzoic acid and polyvinyl alcohol;
3-isocyanato-2,5-dichlorobenzoic acid and cellulose;
3-isocyanato-2,5-dichlorobenzoic acid and chitin;
3-isocyanato-2,5-dichlorobenzoic acid and a 1:1 copolymer of polyvinyl alcohol and polyvinyl acetate;
3-isocyanato-2,5-dichlorobenzoic acid and polyvinyl amine;
3-isocyanato-2,5-dichlorobenzoic acid and dextran (average molecular weight 70,000).

In addition to the pesticide-polymer systems of the present invention which are prepared by reacting an isocyanate derivative of a pesticide with a polymer, there are other similar pesticide-polymer systems which may be prepared by the polymerization of a suitable pesticide-monomer adduct.

The pesticide monomer adduct may be prepared by reacting a monomer having a vinyl or similar polymerizable group with an isocyanate derivative of a pesticide and then polymerizing the resulting pesticide-monomer adduct.

The reaction may be illustrated as follows:

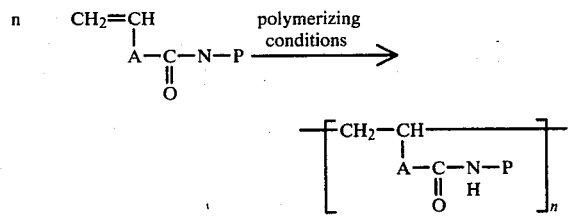

in which n is 5 or more.

The above described pesticide-polymer systems can be represented by the previously given generic formula:

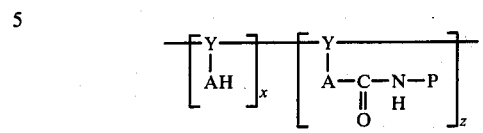

in which x is 0 and z is n and all other symbols are as previously depicted.

In addition to the linear polymer systems described, cross-linked systems may be prepared by adding a multifunctional isocyanate with the P-NCO to the preferred polymer reactant to yield network systems. Suitable multifunctional isocyanates include those disclosed in my previously referred to earlier application which is incorporated by reference herein. Network systems may also be prepared by copolymerizing small amounts of a difunctional of multifunctional vinyl monomer with a pesticide-containing monomer.

The following examples are presented to illustrate the practice of the invention.

EXAMPLE 1

9.69 (0.04 moles) of 4-isocyanato-6-tert-butyl-3-(methylthio)-as-triazine-5(4H) one (prepared by the reaction of 4-amino-6-tert-butyl-3-(methylthio)-as-triazine-5(4H) one with phosgene) is reacted with 10.0 g. of polyvinyl alcohol (99% hydrolyzed, molecular weight 75,000) for 1 hour at 110° C. in 200 ml. of N, N-dimethyl acetamide. The resulting polymer is precipitated into methanol, filtered and dried to yield a pesticide-polymer system as a white solid.

EXAMPLE 2

The procedure of Example 1 is repeated using 0.04 moles of 3-isocyanato-2,5-dichlorobenzoic acid in place of the 4-isocyanato-6-tert-butyl-3-(methylthio)-as-triazin-5(4H) one. The resulting pesticide-polymer system is isolated in a similar manner.

EXAMPLE 3

9.69 (0.04 moles) of 4-isocyanato-6-tert-butyl-3-(methylthio)-as-triazine-5(4H) one is reacted with 10.0 g. of polyvinyl alcohol (99% hydrolyzed, molecular weight 20,000) for 1 hour at 110° C. in 200 ml. of N, N-dimethyl acetamide. The resulting polymer is precipitated into methanol, filtered and dried to yield the pesticide-polymer system as a white solid.

EXAMPLE 4

The procedure of Example 3 is repeated using 0.04 moles of 3-isocyanato-2,5-dichlorobenzoic acid in place of the 4-isocyanato-6-tert-butyl-3-(methylthio)-as-triazine-5(4H) one. The resulting pesticide-polymer system is isolated in a similar manner.

EXAMPLE 5

9.69 (0.04 moles) of 4-isocyanato-6-tert-butyl-3-(methylthio)-as-triazine-5(4H) one is reacted with 10.0 g. of cellulose for 1 hour at 110° C. in 200 ml. of dimethyl sulfoxide. One half of the solvent is removed and then the resulting polymer is precipitated into methanol, filtered and dried to yield the desired pesticide-polymer system.

EXAMPLE 6

The procedure of Example 5 is repeated using 0.04 moles of 3-isocyanato-2,5-dichlorobenzoic acid in place of the 4-isocyanato-6-tert-butyl-3-(methylthio)-as-triazine-5(4H) one. The resulting pesticide-polymer system is isolated in a similar manner.

EXAMPLE 7

9.69 (0.04 moles) of 4-isocyanato-6-tert-butyl-3-(methylthio)-as-triazine-5(4H) one is reacted with 5.0 g. of chitin (poly N-acetyl glucosamine) for 1 hour at 110° C. in 200 ml. of dimethyl sulfoxide. One half of the solvent is removed and the resulting polymer is precipitated into methanol, filtered and dried to yield the desired pesticide-polymer system.

EXAMPLE 8

The procedure of Example 7 is repeated using 0.04 moles of 3-isocyanato-2,5-dichlorobenzoic acid in place of the 4-isocyanato-6-tert-butyl-3-(methylthio)-as-triazine-5(4H) one. The resulting pesticide-polymer system is isolated in a similar manner.

EXAMPLE 9

9.69 (0.04 moles) of 4-isocyanato-6-tert-butyl-3-(methylthio)-as-triazine-5(4H) one is reacted with 10.0 g. of a 1:1 copolymer of polyvinyl alcohol and polyvinyl acetate for 1 hour at 110° C. in 200 ml. of N, N-dimethyl acetamide. The resulting polymer is precipitated into methanol, filtered and dried to yield the pesticide-polymer system as a white solid.

EXAMPLE 10

The procedure of Example 9 is repeated using 0.04 moles of 3-isocyanato-2,5-dichlorobenzoic acid in place of the 4-isocyanato-6-tert-butyl-3-(methylthio)-as-triazine-5(4H) one. The resulting pesticide-polymer system is isolated in a similar manner.

EXAMPLE 11

The procedure of Example 9 is repeated using 10.0 g. of polyvinyl amine in place of the copolymer. The resulting polymer is isolated in a related manner.

Polymers from the above examples may contain 20-50% pesticide by weight based on the final weight after drying. By proper adjustment of reactants, systems can be prepared containing up to 60% or so of pesticide by weight. If desired, additives such as u.v. stabilizers, fillers and the like can be added to obtain pesticide-polymer systems with a wide range of physical properties tailored to specific needs.

In order to evaluate the controlled or sustained release of the pesticidal material from the pesticide-polymer systems, the following tests were performed:

1. Samples from the above described experiments were tested for release in distilled $H_2O$ over a period of weeks;
2. Aliquots were removed periodically and tested by:
   a. u.v. ($H_2O$ solution directly); and
   b. gas chromatography on extracted portions;
3. Samples were carefully weighed prior to water immersion; weighed after test; and
4. Soil tests were conducted.

The results of the tests indicated the amount of active pesticidal material in each instance which is released on a controlled and sustained manner over an extended period of time.

Tests also were performed to demonstrate that the chemically bonded compositions of the present invention provide a more controlled and sustained release of the pesticide than is obtained with physical mixtures of the ingredients or by use of the pesticide alone. The results of some of those tests are summarized below and are reported in detail in my article entitled "Homogeneous Solution Reactions of Cellulose, Chitin, and Other Polysaccharides to Produce Controlled Activity Pesticide Systems" J. Poly Sci., Polymer Letters, ed. August, 1978.

In the tests, metribuzin was chosen as the model pesticide because of its high activity at relatively low concentrations, its selectivity, its lack of persistence in the environment, its high mobility and its amino group which is readily converted to an isocyanato group upon reaction with phosgene. Polyvinyl alcohol, chitin, cellulose, amylose, amylopectin, dextran and starch were selected as the polymers because they are biodegradable and readily available.

The pesticide-polymers were typically prepared by reacting 1.0 g. of the chosen polysaccharide polymer dissolved in a solvent mixture of N,N-dimethylacetamide and 5% lithium chloride or lithium nitrate to which the isocyanato derivative of metribuzin in the N,N-dimethylacetamide was added dropwise. Upon completion of the reaction as monitored by disappearance of the isocyanato absorbance in the infrared spectra the products were isolated by precipitation of the reaction solution into methanol and purified by Sophlet extraction.

The physical data for the pesticide-polymers described above are shown in Table I. Pendant pesticide attachment was confirmed by comparison of each synthesized system with a mixture of the unreacted polysaccharide and the pesticide using a Waters Model ACL-200 Liquid Chromatograph with porous glass bead columns and a 5% $LiNO_3$/DMAc solvent. A comparison of the retention times along with the ultraviolet and refractive index absorbances revealed no detectable unattached pesticide in the samples. Identification of the carbamate polymer-to-pesticide bonds was made using a Perkin Elmer 257 Grating Infrared Spectrophotometer.

The viscosity data are reported in Table I for a number of controlled activity systems in 5% LiCl/DMAc. At low concentrations, an upward curvature in the plot of the $N_{sp/c}$ vs. c curve was observed, making intrinsic viscosity determination impractical. Therefore, reduced viscosities at 0.25 g/dl are recorded. This concentration dependence is likely due to intermolecular complexation of hydroxyl functionality on the polysaccharides with the lithium ions.

TABLE I.

Physical Properties of Polysaccharides with Pendant Pesticides

| Structure | Herbicide wt. % | D.S.$^a$ | % Yield | IR Absorbance (cm$^{-1}$), Bond | $N_{sp/c}$ @ 0.25 g.dl |
|---|---|---|---|---|---|
| CHI—C(=O)—R$_1$ | 47 | 0.91 | 98 | 1700, carbamate | 0.52 |
| CEL—C(=O)—R$_1$ | 57 | 1.2 | 88 | 1700, carbamate | 0.55 |
| AM—C(=O)—R$_1$ | 57 | 1.2 | 85 | 1700, carbamate | 0.58 |

TABLE I.-continued

Physical Properties of Polysaccharides with Pendant Pesticides

| Structure | Herbicide wt. % | D.S.[a] | % Yield | IR Absorbance (cm$^{-1}$), Bond | sp/$c$ @ 0.25 g.dl |
|---|---|---|---|---|---|
| AMP—O—C(=O)—R$_1$ | 47 | 0.75 | 12 | 1700, carbamate | 0.25 |
| D—O—C(=O)—R$_1$ | 51 | 0.90 | 87 | 1700, carbamate | 0.46 |
| S—O—C(=O)—R$_1$ | 57 | 1.2 | 83 | 7000, carbamate | 0.56 |

CHI = Chitin
CEL = Cellulose
AM = Amylose
AMP = Amylopectin
D = Dextran
S = Starch
R$_1$ = Metribuzin Remainder
[a]Degree of Substitution Pesticide release was monitored as a function of time for each polymer. A 0.05 g sample was placed in 20 ml of distilled water. Samples (10 hl) were withdrawn at designated intervals and injected into a Waters ALC-200 Liquid Chromatograph with Bondapak ® column with ultraviolet and refractive index detectors. Concentration of pesticide present in the water was then determined by comparison with standard curves. The concentrations of pesticide after 0.1, 8, 24, and 48 hours are reported in Table II for three samples with metribuzin pendant groups. Due to significant rates of hydrolytic decomposition, the total amount of pesticide released is not accurately described by the observed solution concentration. For example, additional hydrolysis products of polymers with metribuzin pendant groups were shown by an increase in the number of observable peaks at extended times. These peaks correspond to those generated from hydrolysis of pure metribuzin under similar conditions. It may be concluded, therefore, that both pesticide release from the polymer and pesticide hydrolysis occurred during the 48 hour study.

Results indicate that rates of pesticide release in water are dependent upon the nature of the polymer-to-pesticide bond, the hydrophilicity of the polymer, particle size, and pH. As surface bonds are hydrolyzed in these systems, the decrease in available pendant pesticide and simultaneous decomposition of the pesticide in solution result in a gradual reduction in observed concentration with time.

The release of an effective amount of active pesticide can be controlled by the ratio of pesticide to polymer substrate and the nature of the polymer substrate. The amount of pesticide that is chemically bonded to the polymer and the type of bonding dictates the time which is needed to release effective amounts of the active pesticides.

The exposure of a viable form of plant to the action of the herbicidal compositions disclosed can give rise to different responses depending upon the nature of the plant, its maturity, the amount of herbicidal composition used, the release rate of the active herbicide and the particular herbicide employed. Application to plants and plant parts of an herbicidal amount of the herbicide compositions suppresses and inhibits growth of such plants. Application of the herbicide compositions may be made by mulching or disking the compositions into the soil or merely by applying the composition to the surface of the soil. The exact dosage applied depends on the release rate of the composition, the vegetation to be controlled and the herbicide employed.

The pesticide-polymers of the present invention are novel, useful products which can be used in the same manner as conventional pesticides. For example, they can be powdered, granulated and sprayed, dusted or otherwise applied to: (1) reduce environmental pollution by reducing pesticide mobility, (2) reduce the number of applications required during the growing season, and/or (3) result in enhanced agricultural production.

It will be readily apparent to those skilled in the art that a number of modifications and changes can be made without departing from the spirit and scope of the present invention. Therefore, it is not intended that the invention be limited by the illustrative examples, but only by the claims which follow.

I claim:

1. A pesticide-polymer having a macromolecular backbone with pendant pesticidal groups chemically linked thereto by linkages which are broken under environmental conditions of use to controllably release an effective amount of active pesticide, which pesticide-polymer is prepared by reacting a polymer having pendant hydroxy groups, said polymer being selected from polyvinyl alcohol and polyvinylalcohol copolymers, with a pesticide derivative having an —NCO group, said pesticide derivative having been prepared from a pesticide having an —NH$_2$ group.

2. A pesticide-polymer of claim 1 in which the polymer is polyvinyl alcohol.

3. A pesticide-polymer of claim 2 in which the pesticide derivative is 4-isocyanato-6-tert-butyl-3-(methylthio)-as-triazine-5(4H) one.

4. A pesticide-polymer of claim 2 in which the polymer is polyvinyl alcohol and the pesticide derivative is 4-isocyanato-6-tert-butyl-3-(methylthio)-as-triazine-5(4H) one.

5. A pesticide-polymer of claim 4 in which the pesticide derivative is 3-isocyanato-2,5-dichlorobenzoic acid.

* * * * *